United States Patent
Bondinell et al.

Patent Number: 6,028,087
Date of Patent: Feb. 22, 2000

[54] PLATELET AGGREGATION INHIBITING COMPOUNDS

[75] Inventors: William Edward Bondinell, Wayne; James Francis Callahan, Philadelphia; William Francis Huffman; Richard McCulloch Keenan, both of Malvern; Brian Walter Metcalf, Radnor; James Samanen, Phoenixville; Tobias Oregon Yellin, Villanova, all of Pa.

[73] Assignee: SmithKline Beecham Corporation, Philadelphia, Pa.

[21] Appl. No.: 09/010,238

[22] Filed: Jan. 21, 1998

Related U.S. Application Data

[62] Division of application No. 08/464,728, filed as application No. PCT/US93/12530, Dec. 22, 1993, Pat. No. 5,726,192.

[51] Int. Cl.[7] ............ C07D 213/73; A61K 31/44
[52] U.S. Cl. ............................. 514/357; 546/336
[58] Field of Search .................. 546/309, 336; 514/352, 357

[56] References Cited

U.S. PATENT DOCUMENTS

| | | | |
|---|---|---|---|
| 4,208,430 | 6/1980 | Bondinell et al. | 424/326 |
| 4,672,066 | 6/1987 | Carson et al. | 514/256 |
| 4,874,864 | 10/1989 | Bondinell et al. | 546/153 |

FOREIGN PATENT DOCUMENTS

A1 0 381 033  1/1990  European Pat. Off. .

OTHER PUBLICATIONS

Windholz et al, The Merck Index, p. 1007, Monograph 6880, 1983.

Chemical Abstracts, vol. 88, No. 9, Abstract 62,415q, 1978, p. 392.

Chemical Abstracts, vol. 112, No. 7, Abstract 52,576r, 1990, p. 841.

*Primary Examiner*—Zinna Northington Davis
*Attorney, Agent, or Firm*—Mary E McCarthy; Stephen Venetianer; Charles M Kinzig

[57] ABSTRACT

Compounds of the formula (I):

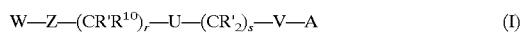

wherein:

A is

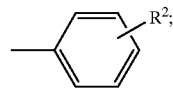

W is (N);

Z is $(CH_2)_{1-2}$;

U and V independently are present as CO, $CR'_2$, $C(=CR'_2)$, $S(O)_r$, O, NR', CR'OR', $CR'(OR'')CR'_2$, $CR'_2CR'(OR'')$, $C(O)CR'_2$, $CR'_2C(O)$, CONR', NR'CO, OC(O), C(O)O, C(S)O, OC(S), C(S)NR', NR'C(S), $S(O)_rNR'$, $NR'S(O)_r$, N=N, NR'NR', $NR'CR'_2$, $NR'CR'_2$, $CR'_2O$, $OCR'_2$, C≡C, CR'=CR', or $CR'(NR'R'')C(O)$;

each r independently is 0 to 3;

s is 0 to 2;

each R' independently is H, $C_{1-4}$alkyl, $C_{3-7}$cycloalky-$C_{0-4}$alkyl, or Ar-$C_{0-4}$alkyl;

each R" independently is R', —C(O)R', or —C(O)$OR^{15}$;

$R^{10}$ is H, $C_{1-4}$alkyl, or —NR'R';

each $R^{15}$ independently is $C_{1-4}$alkyl, $C_{3-7}$cycloalkyl-$C_{0-4}$alkyl, or Ar-$C_{0-4}$alkyl;

$R^2$ is present once or twice as $C_{1-4}$alkyl, J—$CO_2R'$, CONR', SR', NR'R", $C_{1-4}$alkoxy, hydroxy, CN, $CF_3$, halo, or

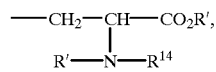

with the proviso that at least one $R^2$ is J—$CO_2R$; and J is a single bond, —$OCR'_2$—, —$NR'CR'_2$—, $CR'_2$—$CR'_2$—, —$CR'_2$—, —CR'=CR', or —C(O)NR'$CR'_2$—;

each $R^{14}$ independently is $C_{1-4}$alkyl, $C_{3-7}$cycloalkyl-$C_{0-4}$alkyl, Ar-$C_{0-4}$alkyl, C(O)R', CN, $NO_2$, $SO_2R'$, or C(O)$OR^{15}$;

or a pharmaceutically acceptable salt thereof, are effective for inhibiting platelet aggregation.

8 Claims, No Drawings

PLATELET AGGREGATION INHIBITING COMPOUNDS

This is a divisional of application Ser. No. 08/464,728 filed Aug. 8, 1995, now U.S. Pat. No. 5,726,142 which is a 371 of PCT/US93/12530 filed Dec. 22, 1993.

FIELD OF THE INVENTION

This invention relates to novel compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence (RGD in single letter amino acid code). Von Willebrand factor and fibrinogen, which are considered to be natural ligands for the GPIIb-IIIa receptor, possess an RGD sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g. inhibitors of the GPIIb-IIIa protein) which have potent in vivo and in vitro effects and lack the peptide backbone structure of amino acid sequences.

The present invention discloses novel compounds. These compounds inhibit binding to the GPIIb-IIIa receptor and inhibit platelet aggregation.

SUMMARY OF THE INVENTION

In one aspect this invention is a novel compound as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, myocardial infarction, or atherosclerosis.

DETAILED DESCRIPTION OF THE INVENTION

This invention discloses novel compounds which inhibit platelet aggregation. The novel compounds are believed to interact favorably with the GPIIb-IIIa receptor and to orient the substituent sidechains on the six and five membered rings so that they may also interact favorably with the receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

$$W-(CR'_2)_q-Z-(CR'R^{10})_r-U-(CR'_2)_s-V-(Gly)_n-(Asp)_m-A \qquad (I)$$

wherein:

W is R'R"N—, R'R"NR'N—, R'R"NR'NCO—, R'$_2$NR'NC(=NR')—, R'ONR'C(=NR')—,

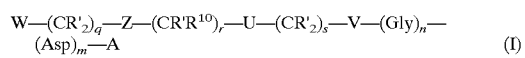

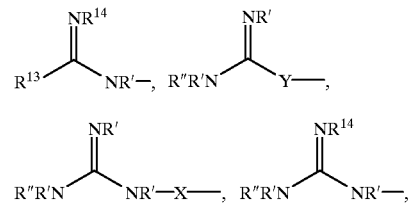

or Ⓝ;

Z is (CH$_2$)$_t$, Het, Ar, C$_{3-7}$cycloalkyl, or NR';

U and V independently are absent or present as CO, CR'$_2$, C(=CR'$_2$), S(O)$_t$, O, NR', CR'OR', CR'(OR")CR'$_2$, CR'$_2$CR'(OR"), C(O)R'$_2$, CR'$_2$C(O), CONR', NR'CO, OC(O), C(O)O,C(S)O,OC(S), C(S)NR', NR'C(S), S(O)$_t$NR', NR'S(O)$_t$, N=N, NR'NR', NR'CR'$_2$, NR'CR'$_2$, CR'$_2$O, OCR'$_2$, C≡C, CR'=CR', or CR'(NR'R")C(O);

X is N=CR', C(O), or O;

Y is S or O;

m is 0 or 1;

n is 0 or 1;

q is 0 to 3;

each r independently is 0 to 3;

s is 0 to 2;

each t independently is 0 to 2;

each R' independently is H, C$_{1-4}$alkyl, C$_{3-7}$cycloalkyl-C$_{0-4}$alkyl, or Ar-C$_{0-4}$alkyl;

each R" independently is R', —C(O)R', or —C(O)OR$^{15}$;

R$^{10}$ is absent or present as H, C$_{1-4}$alkyl, or -NR'R';

each R$^{13}$ independently is R', CF$_3$, S', or OR';

each R$^{14}$ independently is C$_{1-4}$alkyl, C$_{3-7}$cycloalkyl-C$_{0-4}$alkyl, Ar-C$_{0-4}$alkyl, C(O)R', CN, NO$_2$, SO$_2$R', or C(O)OR$^{15}$;

each R$^{15}$ independenly is C$_{1-4}$alkyl, C$_{3-7}$cycloalkyl-C$_{0-4}$alkyl, or AR-C$_{0-4}$alkyl;

A is

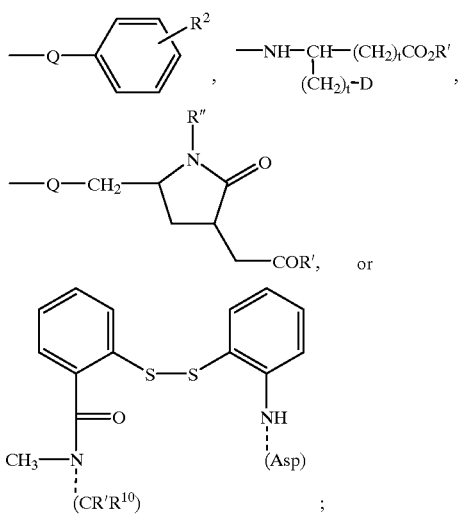

$R^2$ is absent or present once or twice as $C_{1-4}$alkyl, J—$CO_2R'$, $CONR'$, $SR'$, $NR'R''$, $C_{1-4}$alkoxy, hydroxy, CN, $CF_3$, halo, or

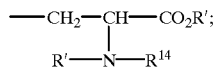

J is a single bond, —$OCR'_2$—, —$NR'CR'_2$—, $CR'_2$—$CR'_2$—, —$CR'_2$—, —$CR'$=$CR'$, or —$C(O)NR'CR'_2$—;

Q is a single bond, $CR'_2$, S, O, or NR'; and

D is $C_{1-4}$alkyl, $C_{3-7}$cycloalkyl, Ar, or Het; or a pharmaceutically acceptable salt thereof, provided that:

(i) when A is

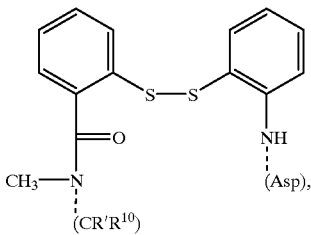

then W—$(CR'_2)_q$—Z—$(CR'R^{10})_r$— is not $H_2N$—$(CH_2)_{3-5}$—CH—;

(2) when A is

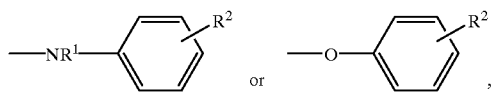

then W—$(CR'_2)_q$—Z—$(CR'R^{10})_r$— is not NHR'; and (3) when A is

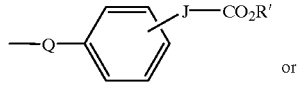

-continued

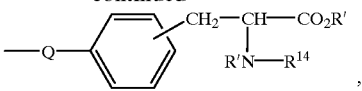

then W—$(CR'_2)_q$—Z—$(R'R^{10})_r$— is not

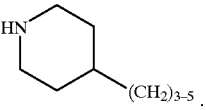

Also included in this invention are complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

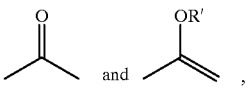

and tautomers of guanidine-type groups, such as

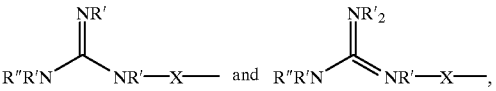

each tautomeric form is contemplated as being included within this invention whether existing in equilibrium or locked in one form by appropriate substitution with R'. The meaning of any substituent at any one occurrence is independent of its meaning, or any other substituent's meaning, at any other occurrence, unless specified otherwise.

With reference to formula (I), suitably,
Z is Het;
m, n, and q are each 0; and
A is

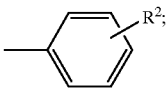

W is R'R''N—;
at least one $R^2$ on the A group defined as phenyl is J—$CO_2R$.

Particular compounds of the invention encompassed by the above-defined subgeneric of formula (I) include, but are not limited to, the following:

4-[2-[3-[6-amino-2-pyridinyl]-1-oxopropyl-(methyl)amino]-1-oxoethyl]phenoxyacetic acid;

4-[2-[4-[6-amino-2-pyridinyl]-1-oxobutyl-(methyl)amino]-1-oxoethyl]phenoxyacetic acid; and 4-[[N-methyl-N-[5-(2-aminobenzimidazolyl)]amino]acetyl]-2,2'-[1,2-phenylenebis(oxy)]bisacetic acid; or a pharmaceutically acceptable salt thereof.

Also, with reference to formula (I), suitably,
Z is $(CH_2)_{1-2}$;
m, n, and q are each 0;
A is

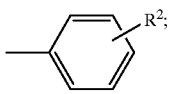

W is Ⓝ; and at least one $R^2$ on the A group defined as phenyl is J—$CO_2R'$.

A particular compound of the invention encompassed by the above-defined subgeneric of formula (I) includes, but is not limited to, 4-[[N-methyl-N-[3-(4-pyridinyl)propionyl]amino]acetyl]-2,2'-[1,2-phenylenebis(oxy)bisacetic acid or a pharmaceutically acceptable salt thereof.

Also, with reference to formula (I), suitably,
Z is $(CH_2)_{1-2}$ or phenyl;
r and s are each 0;
m and n are each one;
V is absent;
A is

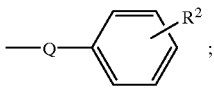

and W is

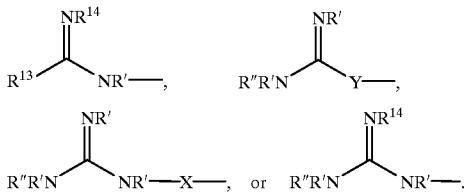

Particular compounds of the invention encompassed by the above-defined subgeneric of formula (I) include, but are not limited to, the following:
$N^\alpha$-acetyl-caravaninyl-glycinyl-aspartyl-anilide;
$N^\alpha$-benzoyl-N(quanidino)cyano-$N^\alpha$-methyl-L-arginylglycyl-L-aspartic-1-anilide; and
$N^\alpha$-benzoyl-$N^\Delta$-[cyanoimino)(phenoxy)methyl]-$N^\alpha$-methyl-L-ornithylglycyl-L-aspartic-1-anilide.

Also, with reference to formula (I), suitably,
Z is Het;
m and n are each one;
V is absent;
A is

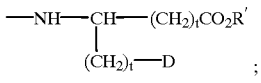

and W is R'R"N—.

Particular compounds of the invention encompassed by the above-defined subgeneric of formula (I) include, but are not limited to, the following:
3-[6-amino-2-pyridinyl]propionyl-glycyl-L-aspartyl-L-phenylalanine; and
4-[6-amino-2-pyridinyl]buturyl-glycyl-L-aspartyl-L-phenylalanine or a pharmaceutically acceptable salt thereof.

Also, with reference to formula (I), suitably,
Z is $(CH_2)_{1-2}$ or NR';
A is

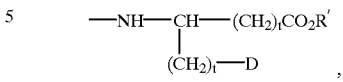

wherein D is Het; and W is Ⓝ,

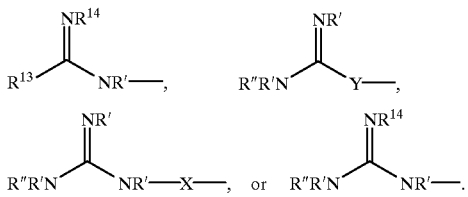

Particular compounds of the invention encompassed by the above-defined subgeneric of formula (I) include, but are not limited to, the following:
$N^\alpha$-benzoyl-$N^\Delta$-[1H-imidazol-2-yl)L-ornithylglycyl-$\beta$(2-benzothiazolyl)$\beta$-alanine; and
±-N-[4-quanidinoamino)butanoylsarcosinyl]-$\beta$-(2-benzothiazolyl)-$\beta$-alanine; or a pharmaceutically acceptable salt thereof.

Also, with reference to formula (I), suitably,
Z is Ar or Het;
m and n are each one;
s is zero;
V is absent; and
W is R"R'N—.

A particular compound of the invention encompassed by the above-defined subgeneric of formula a) includes, but is not limited to cyclo-(S,S)-(2-mercapto)benzoyl-N$\alpha$-methyl)-4-aminomethylphenylalanyl-glycyl-aspartyl-(2-mercapto)phenylamide.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

Arg refers to arginine, MeArg refers to $N^\alpha$-methyl-arginine, HArg refers to homoarginine, NArg refers to norarginine, ($Me_2$)Arg refers to N',N"-dimethyl arginine, ($Et_2$)Arg refers to N',N"-diethyl arginine and Orn refers to ornithine. These radicals are suitable components of the substituent $R^6$. $N^\alpha$-Substituted derivatives of these amino add are also useful in this invention. Representative methods for preparing α-substituted derivatives are disclosed in U.S. Pat. No. 4,687,758; Cheung et al., *Can. J. Chem.*, 55, 906 (1977); Freidinger et al., *J. Org. Chem.*, 48, 77, (1982); and Shuman et al., PEPTIDES: PROCEEDINGS OF THE 7TH AMERICAN PEPTIDE SYMPOSIUM, Rich, D., Gross, E., Eds, Pierce Chemical Co., Rockford, Ill.,617 (1981), which are incorporated herein by reference.

$C_{1-4}$alkyl as applied herein means carbon chains which are branched or unbranched and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g. that a covalent bond is present).

Ar, or aryl, as applied herein, means phenyl or naphthyl, or phenyl or naphthyl substituted by one to three moieties $R^2$. In particular, $R^2$ may be $C_{1-4}$alkyl, $C_{1-4}$alkoxy, $C_{1-4}$alkylthio, trifluoroalkyl, OH, Cl, Br, F, or J—$CO_2$H, wherein J is as defined in formula (I).

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are imidazole, benzimidazole, pyrrole, indole, pyridine, pyrimidine, pyraine, quinoline, benzofuran, furan, benzopyranan, benzothiophene, thiophene, thiazole, benzothiazole indoline, morpholine, piperidine, piperazine, pyrrolidine, isoquinoline, and tetra- and perhydro-quinoline and isoquinoline. Any accessible combination of up to three substituents, such as chosen from $R^2$, on the Het ring that is available by chemical synthesis and is stable is within the scope of this invention.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $R^2$, on the cycloalkyl ring that is available by conventional chemical synthesis and is stable, is within the scope of this invention.

$\overset{N}{\bigcirc}$ as used herein indicates a nitrogen heterocycle, which may be a saturated or an unsaturated stable five-, six- or seven-membered monocyclic ring or a seven- to ten-membered bicyclic ring, containing up to three nitrogen atoms or containing one nitrogen atom and a heteroatom chosen from oxygen and sulfur, and which may be substituted on any atom that results in a stable structure, and wherein the nitrogen heteroatom may be optionally quaternized. The nitrogen heterocycle may be substituted in any stable position by $C_{1-4}$alkoxy, $C_{1-4}$alkylthio, F, Cl, Br, I, $NO_2$, $NR'_2$, OH, $CO_2R'$, CONHR', or $C_{1-4}$alkyl. Representative of $\overset{N}{\bigcirc}$ are pyrroline, pyrrolidine, imidazole, imidazoline, imidazolidine, pyrazole, pyrazoline, pyrazolidine, piperidine, piperazine, morpholine, pyridine, pyridinium, tetrahydropyridine, tetrahydro- and hexahydro-azepine, quinuclidine, quinuclidiniuim, quinoline, isoquinoline, and tetra- and perhydro-quinoline and isoquinoline. In particular, $\overset{N}{\bigcirc}$ may be pyridinyl, imidazolyl, pyrolidinyl, piperidinyl, piperazinyl, or tetrahydropyridinyl.

t-Bu refers to the tertiary butyl radical, Boc refers to the t-butyloxycarbonyl radical, Fmoc refers to the fluorenyl-methoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. MeArg is $N^\alpha$-methyl arginine.

DCC refers to dicyclohexylcarbodiimide, DMAP refers to dimethylaminopyridine, DIEA refers to diisopropylethyl amine, EDC refers to N-ethyl-N'(dimethylaminopropyl) carbodiimide. HOBt refers to 1-hydroxybenzotriazole, THF refers to tetrahydrofuran, DIEA refers to diisopropylethylamine, DMF refers to dimethyl formamide, NBS refers to N-bromo-succinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylmino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (II) with a compound of the formula (III):

A—(Gly)$_n$(Asp)$_m$—L$^1$      (II)

R$^{6''}$—L$_2$      (III)

wherein A, m, and n are as defined in formula (I), with any reactive functional groups protected;

$L^1$ and $L^2$ are functional groups which are capable of reacting to form the linkage —(CR'R$^{10}$)$_r$—U—(CR'$_2$)$_s$—V—; and $R^{6''}$ is W—(CR'$_2$)$_q$—Z— and any portion of the group —(CR'R$^{10}$)$_r$—U—(CR'$_2$)$_s$—V— which is connected to $L^2$, with any reactive functional groups protected;

and thereafter removing any protecting groups, and optionally forming a pharmaceutically acceptable salt.

It will be apparent that the precise identity of $L^1$ and $L^2$ will be dependent upon the site of the linkage being formed. General methods for preparing the linkage —(CR'R$^{10}$)$_r$—U—(CR'$_2$)$_s$—V— are described, for example, in EP-A 0 372 486 and EP-A 0 381 033 and EP-A 0 478 363, which are incorporated herein by reference.

For instance, if V is CONH, $L^1$ may be —NH$_2$, $L^2$ may be OH (as in an acid) or Cl (as in an acid chloride), and $R^{6''}$ may be W—(CR'$_2$)$_q$—Z—(CR'R$^{10}$)$_r$—U—(CR'$_2$)$_s$—C(O) with any functional groups optionally protected. For example, $R^{6''}$ may be (benzyloxycarbonyl-amidino)benzoyl- or ($N^\alpha$-Boc,$N^{guan}$-Tos)arginyl-. When $L^2$ is OH, a coupling agent is used.

Similarly, if V is NHCO, $L^1$ may be —$CO_2$H or CO—Cl, $L^2$ may be —NH$_2$, and $R^{6''}$ may be W—(CR'$_2$)$_q$—Z—(CR'R$^{10}$)$_r$—U—(CR'$_2$)$_s$—. For example, $R^{6''}$ may be (benzyloxycarbonyl-amidino)phenyl, (benzyloxycarbonylamino)methylbenzyl- or 6-(benzyloxycarbonylamino)hexyl-.

Where V is NHSO$_2$, $L^1$ may be SO$_2$Cl, $L^2$ may be —NH$_2$ and $R^{6''}$ may be as above. Where V is SO$_2$NH, $L^1$ may be —NH$_2$ and $L^2$ may be SO$_2$Cl. Methods to prepare such sulfonyl chlorides are disclosed, for instance, in J. Org. Chem., 23, 1257 (1958).

If V is CH=CH, $L^1$ may be —CHO, $L^2$ may be CH=P—Ph$_3$ and $R^{6''}$ may be W—(CR'$_2$)$_q$—Z—(CR'R$^{10}$)$_r$—U—(CR'$_2$)$_s$—.

Where V is CH$_2$CH$_2$ may be obtained by reduction of a suitably protected compound wherein V is CH=CH.

Where V is CH$_2$O, CH$_2$N or, $L^1$ may be —OH, —NH or -, respectively; $L^2$ may be —Br; and $R^{6''}$ may be W—(CR'$_2$)$_q$—Z(CR'R$^{10}$)$_r$—U—(CR'$_2$)$_s$—. For example, $R^{6''}$ may be (benzyloxycarbonylamino)-methylbenzyl- or 2-(N-benzyl4-piperidinyl)-ethyl. Similarly where U or V is OCH$_2$, NR'CH$_2$ or, $L^1$ may be —CH$_2$Br, and $L^2$ may be —OH, —NH or -, respectively.

Compounds wherein V is CHOHCH$_2$ may be prepared from a suitably protected compound where V is CH=CH by the procedure disclosed in J. Org. Chem., 54, 1354 (1989).

Compounds wherein V is CH$_2$CHOH may be obtained from a suitably protected compound where V is CH=CH by hydroboration and basic oxidation as disclosed in Tet. Lett., 31, 231 (1990).

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.,* 29, 984 (1986) and *J. Med. Chem.,* 30, 2291 (1987) are generally illustrative of the technique and are incorporated herein by reference.

Solution synthesis for the formation of amide or peptide bonds is accomplished using conventional methods used to form amide bonds. Typically, the amine or aniline is coupled via its free amino group to an appropriate carboxylic acis substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

Compounds of formula (III) are prepared by conventional methods known in the art from commercially available materials. W is a generally a basic functional group attached to Z, optionally via an alkyl chain, and is protected during the synthesis or is introduced into the molecule after the —(CR'R$^{10}$)$_r$—U—(CR'$_2$)$_s$—V— linkage has been formed. For example, compounds of formula (III) or formula (I) wherein W is a suitably substituted R'R"N—, R'$_2$N(R$^{13}$)C=N—, R"N=(R$^{13}$)C—NR'—, R'$_2$N(R'$_2$N)C=N— or R"R'N(R'N=)C—NR', are prepared by conventional methods including those disclosed in EP-A 0 372 486, EP-A 0 381 033 or EP-A 0 478 363, which are incorporated herein by reference.

Compounds of formula (III) wherein W is ⓃⒾ are prepared, inter alia, by methods disclosed in EP-A 0 478 363.

Compounds wherein W is R'$_2$N(R'$_2$N)C=N—X— or R"R'N(R'N=)C—NR'—X—, and X is O are prepared, inter alia, by methods disclosed in *J. Org. Chem.,* 51, 5047 (1986).

Compounds wherein W is R'$_2$N(R'$_2$N)C=N—X— or R"R'N(R'N=)C—NR'—X—, and X is N=CR', are prepared, inter alia, by methods disclosed in U.S. Pat. No. 3,714,253 and *Eur. J. Med. Chem.-Chim. Ther.,* 20, 25 (1985).

Compounds wherein W is R'$_2$N(R'$_2$N)C=N—X— or R"R'N(R'N=)C—NR'—X—, and X is X is C(O), are prepared, inter alia, by methods disclosed in U.S. Pat. No. 3,714,253 and *Can. J. Chem.,* 43, 3103 (1965).

Compounds wherein W is R'ONR'C(=NR') may be prepared, inter alia, by methods disclosed in J. Het. Chem., 16, 1063 (1979) or J. Het. Chem., 26, 125 (1989).

Compounds wherein W is R'$_2$NR'NC(=NR')— are prepared by conventional methods including those disclosed in Syn., 583 (1974).

Compounds wherein W is R'R"NR'N— are prepared, inter alia, by methods disclosed in *J. Prakt. Chem.,* 36, 29 (1967).

Compounds wherein W is R'R"NR'NCO— are prepared, inter alia, by methods disclosed in *Bull. Chem. Soc. Jpn.,* 43, 2257 (1970).

Compounds wherein W is R"R'NC(=NR')Y, and Y is S, are prepared, inter alia, by methods disclosed in *Chem. Lett.,* 1379 (1986).

Compounds of formula (I) or formula (I), wherein W is R"R'NC(=NR')Y and Y is O, are prepared by conventional methods including those disclosed in Japanese Patent 2022751.

The reactive functional groups of the sidechains of each synthetic fragment are suitably protected as known in the art. Suitable protective groups are disclosed in Greene, PROTECTIVE GROUPS IN ORGANIC CHEMISTRY, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (eg. 4-methoxy-benzyl or 2,4-dimethoxy-benzyl) is used to protect the mercapto group or the hydroxyl group. The tosyl group may be used for protection of the imidazolyl group and tosyl or nitro group for protection of the guanidino group. A suitably substituted carbobenzyloxy group or benzyl group may be also be used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or HF treatment, as known in the art.

Compounds of formula (II) wherein A is

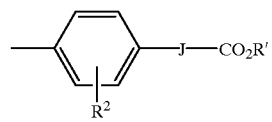

may be prepared by methods disclosed in EP-A 0 381 033, which is incorporated herein by reference.

Compounds of formula (II) wherein A is

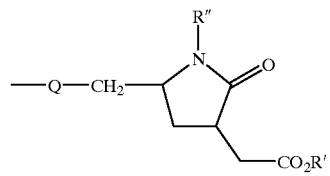

may be prepared by methods disclosed in EP-A 0 483 667, which is incorporated herein by reference.

Compounds of formula (II) wherein A is

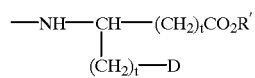

may be prepared by the methods detailed in EP-A 0 319 506, which is incorporated herein by reference.

Compounds of formula (II) wherein A is

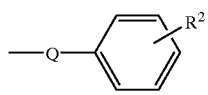

may be prepared by the methods described in WO/08464 and WO 92/13552, which are incorporated herein by reference.

Compounds of formula (II) wherein A is

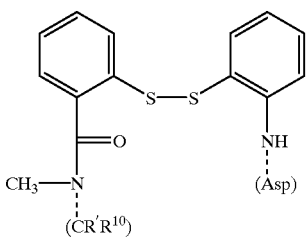

may be prepared by methods disclosed in EP-A 0 425 212, which is incorporated herein by reference.

Acid addition salts of the compounds of formula (I) are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and $NH_4+$ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

This invention also provides a method of inhibiting platelet aggregation and clot formation in a mammal, especially a human, which comprises the internal administration of a peptide of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyperaggregability, such as disseminated intravascular coagulation (DIC), septicemia, surgical or infectious shock, postoperative and postpartum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, and the prevention or treatment of diseases in which bone resorption is a factor.

The compounds of this invention are administered either orally or parenterally to the patient, in a manner such that the concentration of drug in the plasma is sufficient to inhibit platelet aggregation, or other such indication. The pharmaceutical compositions containing the compounds of this invention are administered at a dose between about 0.2 to about 50 mg/kg in a manner consistent with the condition of the patient. For acute therapy, parenteral administration is preferred. For persistent states of hyperaggregability, an intravenous infusion of the compound in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compounds of this invention are administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a compound of formula (I) and a fibrinolytic agent. It has been found that administration of certain compounds in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptolinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophllized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of this invention is administered just prior to, at the same time as, or just after parenteral administration of tPA or other fibrinolytic agent. It may prove desirable to continue treatment with the claimed compounds for a period of time well after reperfusion has been established to maximally inhibit post-therapy reocclusion. The effective dose of tPA, SK, UK or pUK may be from 0.5 to 5 mg/kg and the effective dose of the peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion of the inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor; their ability to inhibit platelet aggregation, in vitro, and their ability to inhibit thrombus formation in vivo.

Inhibition of RGD-mediated GPIIb-IIIa binding

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70 C until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 µglmL polylysine (Sigma Chemical Co., St. Louis, Mo.) at room temperature for 1 h to block nonspecific binding. Various concentrations of unlabeled benzadiazepines were added to the wells in quadruplicate. [$^3$H]-SK&F-107260 was applied to each well at a final concentration of 4.5 nM, followed by the addition of 1 µg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations. The compounds of this invention inhibit [3H]-SK&F 107260 binding with Ki in the range of about 10 μM to about 200 μM.

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at $3\times10^5$ cells/ml. Compounds were added 3 min prior to the agonist in all assays of platelet aggregation. Final agonist concentrations were 0.1 unit/ml thrombin and 2 mM ADP (Sigma). Aggregation was monitored in a Chrono-Log Lumi-Aggregometer. Light transmittance 5 min after addition of the agonist was used to calculate percent aggregation according to the formula % aggregation=[(90-CR) Ö (90-10)]×100, where CR is the chart reading, 90 is the baseline, and 10 is the PRP blank reading. IC50's were determined by plotting [% inhibition of aggregation] vs. [concentration of compound]. Compounds were assayed at 200 mM and diluted sequentially by a factor of 2 to establish a suitable dose response curve.

The compounds of this invention inhibit the aggregation of human platelets stimulated with ADP with IC50 of about 70 to about 200 μM.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins,* 19, 629 (1980).

The examples which follow are intended to in no way limit the scope of this invention, but are provided to illustrate how to make and use the compounds of this invention. Many other embodiments will be readily apparent and available to those skilled in the art.

EXAMPLES

Example 1

4-[2-[3-[6Amino2-pyridinyl]-1-oxopropyl-(methyl)-amino]-1-oxoethyl]]-phenoxyacetic acid (i) 3-(2-[6-Bromopyridyl])propargylalcohol 2,6-Dibromopyridine (15 g, 63 mmol) was placed in a flask and the flask flushed with argon. 200 ml triethylamine was added and the flask was cooled to 0° C. To this was added propargyl alcohol (5 ml, 85 mmol), bis (triphenylphosphine)palladium (II) chloride (1.5 g, 1.4 mmol), and copper iodide (0.50 g, 2.6 mmol). The reaction mixture was stirred at 0° C. or 20 minutes, and was then allowed to warm to room temperature where stirring was continued for 18 hours under argon. After this time the reaction mixture was diluted with ethyl acetate and filtered with ethyl acetate rinses. The solvent was evaporated, and the resulting pale brown solid was chromatographed on silica gel in 70% ethyl acetate/hexane to afford 8 g (59%) of crude product as a pale orange solid. This was tritrated with hexane leaving 6.5 g (48%) of product as a pale yellow solid. NMR ($CDCl_3$): 7.52 ("t", 1H, J=7.8); 7.45 (d, 1H, J=7.8); 7.39 (d, 1H, J=7A); 4.52 (s, 2H). Mass spectrum: 194 ($M+H^+-H_2O$); 212 ($M+H^+$); 234 ($M+Na^+$) An appreciable amount of the bis adduct (2,6di(3-hydroxy-1-propynyl) pyridine) was also observed.

(ii) 3-(2-[6-Bromopyridyl])propan-1-ol 3-(2-[6-Bromopyridyl])-propargylalcohol was reduced using the method of Tilley et al. (JOC, 1988, p.386). (1) (420 mg, 2.0 mmol) was dissolved in 10 ml of ethanol and treated with platinum (IV) oxide hydrate (20 mg, 0.08 mmol) and triethylamine (0.20 ml, 15 mmol). The flask was flushed with H2 and stirred at room temperature under 1 atmosphere of H2 for 90 minutes. The reaction mixture was then filtered through a short silica gel plug using ethyl acetate to remove most of the catalyst. The resulting gray oil was chromatographed using silica gel and 50% ethyl acetate I hexane to yield 310 mg (72%) of the product as a colorless oil. NMR ($CDCl_{13}$): 7.48 ("t", 1H, J=7.7); 7.30 (d, 1H, J=7.8); 7.16 (d, 1H, J=7.5); 4.12 (br, 1H); 3.69 (t, 2H, J=6.2); 2.88 (t, 2H, J=7.5); 1.97 ("q", 2H, J=6.6). Mass spectrum: 198 ($M+H^+-H_2O$); 216 (M+H+); 238 (M+Na+).

(iii) 3-(2-[6-Bromopyridyl])-propionic acid 3-(2-[6-Bromopyridyl])propan-1-ol (1.3 g, 6.0 mmol) was dissolved in 100 ml of acetone and cooled to 0° C. Jones reagent (4.5 ml) was added in three portions at 20 minute intervals. 20 minutes after the addition of the final portion, the reaction was quenched with excess isopropanol and stirred for 10 minutes. The reaction mixture was then diluted with water and roto-evaporated to remove the organic solvents. The remaining aqueous solution was diluted with more water and extracted 4 times with ethyl acetate. The organic layer was rinsed once with brine, dried on sodium sulfate and evaporated leaving 1.1 g (80%) of product as a white solid. NMR ($CDCl_3$): 7.48 ("t", 1H, J=7.8); 7.34 (d, 1H, J=7.9); 7.17 (d, 1H, J=7.5); 3.09 (t, 2H, J=7.2); 2.85 (t, 1H, J=7.2). Mass spectrum: 212 ($M+H^+-H_2O$); 230 (M+H+); 254 (M+Na+).

(iv) 3-(2-[6-Aminopyridyl])-propionic acid

In a three necked flask fitted with a dry ice/acetone condenser and a mechanical stirrer fitted with a glass stir blade was condensed 250 ml of ammonia. To this was added approximately 100 mg of $Fe(NO_3)3.9 H_2O$, and elemental potassium (7.5 g, 190 mmol). The resulting dark blue solution was stirred at reflux for 75 minutes, after which time 3-(2-[6bromopyridyl])-propionic acid (1.2 g, 5.2 mmol) was added in 10 ml of dry THF. After about 10 minutes an additional 10 ml of THF was added. The reaction mixture was refluxed for 6.5 hours and then quenched with 60 g of ammonium chloride. The ammonia was allowed to evaporate overnight. The resulting tan solid was exhaustively extracted with ethyl acetate, and the crude product thus obtained was chromatographed on silica gel using 15% methanol/1% acetic acid/methylene chloride. Obtained 0.47 g (40%) of the desired product as the acetic acid salt. NMR ($CD_3OD$): 7.62 ("t", 1H, J=8.0); 6.64 (d, 1H, J=8.7); 6.60 (d, 1H, J=7.3); 2.92 (t, 2H, J=6.8); 2.60 (t, 2H, J=6.9); 1.94 (br). Mass spectrum: 149 (M+H+–H20); 167 (M+H+). A 13% yield of the bromo amide was also obtained.

(v) 4-[2-[3-[6-Amino-2-pyridinyl]-1-oxopropyl-(methyl)-amino]-1-oxoethyl]-phenoxyacetic acid 3-(2-[6-Aminopyridyl])-propionic acid (95 mg, 0.42 mmol), 4-[2-(methylamino)-1-oxoethyl]phenoxyacetic acid benzyl ester hydrochloride (149 mg, 0.43 mmol) and 1-Hydroxybenzotriazole hydrate (HOBT) (76 mg, 0.56 mmol) were combined in 8 ml of dimethylformamide, and the flask flushed with argon. Diisopropylethylamine (335 μl, 1.9 mmol) was then added and the flask cooled to 0° C. After the mixture had been stirred for five minutes, 1-(3-Dimethylaminopropyl)-3-ethylcarbodiimide hydrochloride (EDC) (103 mg, 0.54 mmol) was added in one portion and the mixture was allowed to warm to room temperature. The mixture was stirred under argon for three days. The dimethylformamide was then removed over the course of several hours using high vacuum. The resulting residue was chromatographed on silica gel using 10% methanol/methylene chloride. The product thus obtained (45 mg, 0.097 mmol) was dissolved in methanol and treated with palladium (10% on carbon) slurried in butanol (16 mg). The flask was flushed with $H_2$, and then stirred under an atmosphere of $H_2$ for several hours at room temperature. The solution was then diluted with isopropanol, filtered, and the solvent removed by roto-evaporation. Reverse phase HPLC gave the desired product as the trifluoroacetate salt in 17% yield for the two steps. NMR ($CD_3OD$): 7.96 (d, 2H, J=8.8); 7.76 ("t", 1H, J=8.1); 7.03 (d, 2H, J=8.8); 6.81 (d, 1H, J=9.0); 6.73 (d, 1H, J=7.3); 4.87 (s, 2H); 4.72 (s, 2H); 3.14 (s, 3H); 3.05 (t, 2H, J=6.1); 2.99 (t, 2H, J=6.5). This set of peaks had a twin set (ratio about 3:1) corresponding to the amide bond conformer. Mass spectrum: 370 (M-H)$^-$; 484 (M+CF3COO—); 741 (2M-H)$^-$. EA: Calculated for $C_{19}H_{21}N_3O_5 \cdot 1.0F_3C_2O_2H \cdot 0.5H_2O$: C, 51.02; H, 4.69; N, 8.50. Found: C, 51.19; H, 4.38; N, 8.14.

Example 2

4-[2-[4-[6-Amino-2-pyridinyl]-1-oxobutyl-(methyl) amino]-1-oxoethyl]-phenoxyacetic acid (i) 4-(2-[6Bromopyridyl])-3-butyn-1-ol A similar reaction was carried out as in Example 1(i) using 3-butyn-1-ol in place of propargyl alcohol. Yield: 49%. NMR ($CDCl_3$): 7A9 ("t", 1H, J=7.7); 7.41 (d, 1H, J=7.8); 7.34 (d, 1H, J=7.3); 3.85 (t, 2H, J=6.1); 2.72 (t, 2H, J=6.2). Mass spectrum: 226 (M+H+); 250 (M+Na+). The bis-adduct was obtained in 16% yield.

(ii) 4-(2-[6-Bromopyridyl])-butan-1-ol

A similar reaction was carried out as in Example 1(ii) on 4-(2-[6-bromopyridyl])-3-butyn-1-ol. Yield: 82%. NMR ($CDCl_3$): 7.46 ("t", 1H, J=7.6); 7.30 (d, 1H, J=7.6); 7.12 (d, 1H, J=7.3); 3.68 (t, 2H, J=6.3); 3.0 (br, 1H); 2.79 (t, 2H, J=7.7); 1.79 (m, 2H); 1.63 (m, 2H). Mass spectrum: 212 (M+H+–H2O); 230 (M+H+); 252 (M+Na+). EA: Calculated for C9H12NOBr C=46.98; H=5.26; N=6.09. Found: C=46.96; H=5.16; N=5.89. The olefin was also obtained in 8% yield.

(iii) 4-(2-[6-Bromopyridyl])-butanoic acid

A similar reaction was carried out as in Example 1(iii) using 4-(2-[6bromopyridyl])-butan-1-ol. Yield: 95%. NMR ($CDCl_3$): 9.9 (br, 1H); 7.48 ("t", 1H, J=7.6); 7.32 (d, 1H, J=7.8); 7.14 (d, 1H, J=7.3); 2.84 (t, 2H, J=7.5); 2.42 (t, 2H, J=7.1); 2.06 ("q", 2H, J=7.3).

(iv) 4-(2-[6-Aminopyridyl])-butanoic acid

A similar reaction was carried out as in Example 1(iv) using 4-2-[6-bromopyridyl])-butanoic acid with the exception that the final purification was by recrystalization from ethyl acetate. Yield: 71%. NMR ($CD_3OD$): 7.58 ("t", 1H, J=8.0); 6.59 (m, 2H); 2.71 (t, 2H, J=7.6); 2.30 (t, 2H, J=7.1); 1.95 ("q", 2H, J=7.3). Mass spectrum: 163 (M+H+–H2O); 181 (M+H+).

(v) 4-[2-[4-[6-Amino-2-pyridiyl]-1-oxobutyl-(methyl) amino]-1-oxoethyl]-phenoxyacetic acid A similar reaction was carried out as in Example 1(v) using 4(2-[(aminopyridyl])-butanoic acid with the exception that following hydrogenation the filtration to remove the catalyst was carried out in 1% acetic acid in water instead of isopropanol. Overall yield: 26%. NMR (DMSO-$d_6$): 7.93 (d, 2H, J=8.7); 7.75 ("t", 1H, J=8.0); 7.62 (br, 1H); 7.4 (d, 2H, J=8.8); 6.73 (d, 1H, J=8.8); 6.66 (d, 1H, J=7.2); 4.83 (s, 2H); 4.81 (s, 2H); 3.36 (br); 3.00 (s,3H); 2.70 (t, 2H, J=7.6); 2.45 (t, 2H, J=7.3); 1.86 (m, 2H). This set of peaks also had a twin set (ratio about 2:1) corresponding to the amide bond conformer. Mass spectrum: 384 (M-H)$^-$; 498 (M+CF3COO—); 769 (2M-H)$^-$. EA: Calculated for $C_{20}H_{23}N_3O_5 \cdot 1.5 F_3C_2O_2H \cdot_2O \; H_2O$: C, 46.63; H, 4.85; N, 7.09. Found: C, 46.25; H, 5.02; N, 6.88.

Example 3

3-[6Amino-2-pyridinyl]-glycyl-(L)-aspartyl-(L)-phenylalanine 3-(2-[6Aminopyridyl])-propionic acid (63 mg, 0.28 mmol), HOBT (50 mg, 0.37 mmol), HCl.H$_2$N-Gly-Asp (OBn)-Phe-OBn (155 mg, 0.28 mmol) and diisopropylethylamine were combined in 7 ml of dry dimethylformamide. The reaction mixture was cooled to 0° C. EDC (68 mg, 0.35 mmol) was added in one portion, the reation mixture allowed to warm to room temperature and placed under argon. After 18 hours, the dimethylformamide was removed on a rotovap at 40° C. The residue was partitioned between ethyl acetate and water, and the organic layer rinsed one time with water, two times with 5% citric acid, once again with water, twice with 5% sodium bicarbonate solution, again with water, and finally one time with brine. The organic solution was dried on sodium sulfate, and the ethyl acetate removed. From this solution was recovered 85 mg (55%) of the starting peptide. The combined aqueous rinses were adjusted to pH 9 using dilute NaOH, and extracted with dichloromethane. Chromatography was carried out on the oil thus obtained on silica gel using 5% methanol/methylene chloride. The product thus obtained (30 mg, 0.5 mmol) was disolved in 5 ml of ethanol, and treated with 10% Pd/C (wetted with butanol) (10 mg). The flask was flushed with H2, and stirred under an atmosphere of H2 for 18 hours. After this time, TLC showed some starting material, so an additional 7 mg of 10% Pd/C was added, and the reation mixture placed again under H2. After 24 additional hours, the solvents were removed using a roto-evaporator, and the residue treated with 1% acetic acid in water. The solution was filtered, and purified using HPLC. This afforded 19 mg of the desired product as a white powder. Overall yield: 10%. NMR ($CD_3OD$): 7.79 ("t", 1H, J=8.1); 7.22 (m, 5H); 6.81 (d, 1H, J=9.0); 6.73 (d, 1H, J=7.2); 4.74 ("t", 1H, J=5.1); 4.61 (m, 1H); 3.85 (s, 2H); 3.18 ("a–b"d, 1H, J=4.5); 3.02 (m, 3H); 2.79 ("a–b"d, 1H, J=5.0); 2.66 (m, 3H). Mass spectrum: 484 (m-H)$^-$, 598 (M+CF3COO—). EA: Calculated for $C_{23}H_{27}N_5O_7 \cdot 2.5H \cdot 2.5H_2O$: C, 41.24; H, 4.22; N, 8.59. Found: C, 41.30; H, 4.26; N, 8.81.

Example 4

4-[6-Amino2-2-pyridinyl]-buturly-glycyl-(L)-aspartyl-(L)-phenylalanine 4-(2-[6-Aminopyridyl])-butanoic acid was treated in a similar manner as in Example 3. Overall yield, 11%. NMR (DMSO-$d_6$): 8.21 (d, 1H, J=8.1); 8.16 (br, 1H); 8.01 (d, 1H, J=7.7); 7.80 ("t", 2H, J=7.9); 7.20 (m, 5H); 6.79 (d, 1H, J=8.8); 6.70 (d, 1H, J=7.3); 4.59 ("q", 1H, J=5.1); 4.36 ("q", 1H, J=5.2); 3.69 (s, 2H); 3.41 (br); 2.97 ("a–b"d, 2H, J=5.2, J=8.5); 2.67 (m, 3H); 2.42 ("a–b", 1H, J=8.3); 2.19 (t, 2H, J=7.1); 1.85 (m, 2H). Mass spectrum: 498 (M-H)$^-$; 612

(M+CF$_3$COO—). EA: Calculated for C$_{24}$H$_{29}$N$_5$O$_7$.2.0F$_3$C$_2$O$_2$H.1.5 H$_2$O: C, 44.57; H, 4.54; N, 9.28. Found: C, 44.84; H, 4.80; N, 8.68.

Example 5

N$^\alpha$- Acetyl-canavaninyl-glycinyl-aspartyl-anilide (i) N$^\alpha$-t-Butyloxycarbonyl-N$^\omega$-t-butyloxycarbonyl-canavanine Canavanine sulfate (5.0 g, 18.2 mmol, Sigma) was dissolved in a mixture of 10% NaOH (aqueous, 50 mL) and t-butyl alcohol (50 mL) and was treated with di-t-butyl-dicarbonate (12.0 g, 55 mmol) at room temperature for 13 d. (reaction complete in 2 d.). The reaction mixture was evaporated under vacuum and then evaporated at reduced pressure from methanol. The crude product was stored as its sodium salt under vacuum and used without further purification: MS (FAB) sodium salt: m/e 398 [(M-H)+Na]$^+$.

(ii) Methyl N$^\alpha$-Butyloxycarbonyl-N$^\omega$-t-butyloxycarbonyl-canavaninyl-glycinate The protected canavanine salt from above in DMF (250 mL) was treated with diisopropylethylamine (19 mL, 109.3 mmol), methyl glycinate hydrochloride (4.58 g, 36.5 mmol, Schweizerhall), 1-hydroxybenzotriazole (4.93 g, 36.5 mmol) and benzotriazol-1-yloxy-tris(dimethylamino) phosphonium hexafluorophosphate (16.1 g, 36.5 mmol) and stirred at room temperature for 24 h. After evaporation under vacuum the residue was purified by repeated flash chromatography (silica gel, 8×20 cm, 2% methanol in chloroform; silica gel, 8×20 cm, 60% ethyl acetate in hexane) to give 3.86 g (47% from canavanine sulfate) of product: $^1$H NMR (CDCl$_3$, 250 MHz) d 1.44 (s, 9H), 1.49 (s, 9H), 1.98–2.13 (m, 2H), 3.77 (s, 3H), 3.93–4.24 (m, 6H), 4.37–4.53 (m, 1H), 5.55–5.68 (m, 1H), 6.31–6.48 (m, 1H), 7.74–7.84 (m, 1H).

(iii) N$^\alpha$-t-Butyloxycarbonyl-γ-benzyl-aspartyl-anilide

N$^\alpha$-t-Butyloxycarbonyl-γ-benzyl-aspartic acid (5.0 g, 15.5 mmol, PRF) was dissolved in DMF (100 mL) and treated with aniline (2.1 mL, 23.3 mmol), 1-hydroxybenzotriazole (2.3 g, 17.1 mmol) and N,N-dicyclohexylcarbodiimide (3.2 g, 15.5 mmol) at room temperature for 24 h. The reaction was filtered and the filtrate evaporated under vacuum. The residue was purified by flash chromatography (silica gel, 6×20 cm, 15% ethyl acetate in hexane) to give 5.70 g (92%) of product: $^1$H NMR (CDCl$_3$) δ 1.45 (s, 9H), 2.60–3.23 (m, 2H), 4.53–4.87 (m, 1H), 5.20 (s, 2H), 5.90 (d, 1H, J=9 Hz), 7.00–7.67 (m, 5H), 7.40 (s, 5H), 8.63 (br s, 1H).

(iv) γ-Benzyl-aspartyl-anilide hydrochloride

N$^\alpha$-t-Butyloxycarbonyl-γ-benzyl-aspartyl-anilide (2.75 g, 6.9 mmol) was treated with 4N HCl in dioxane at room temperature for 4 h. The reaction mixture was evaporated at reduced pressure. The residue was then evaporated first from toluene and then from toluene/methanol and dried under vacuum to give crude product which was used without further purification.

(v) N$^\alpha$-t-Butyloxycarbonyl-N$^\omega$-t-butyloxycarbonyl-canavaninyl-glycine Methyl N$^\alpha$-t-butyloxycarbonyl-N$^\omega$-t-butyloxycarbonyl-canavaninyl-glycinate (1.54 g, 3.45 mmol) in dioxane (10 mL) was treated with 5.2 mL of 1N NaOH (aqueous) at room temperature for 4.5 h. The pH of the reaction mixture was adjusted to 5.5–6.0 (1N aqueous HCl) and then evaporated under vacuum. The residue was evaporated from toluene and dried under vacuum to give product which was used without further purification.

(vi) N$^\alpha$-t-Butyloxycarbonyl-N$^\omega$-t-butyloxycarbonyl-canavaninyl-glycinyl-γ-benzyl-aspartyl-anilide Compounds γ-Benzyl-aspartyl-anilide hydrochloride and N$^\alpha$-t-butyloxycarbonyl-N$^\omega$-t-butyloxycarbonyl-canavaninyl-glycine were dissolved in DMF (200 mL) and treated with diisopropylethylamine (3.61 mL, 20.7 mmol), 1-hydroxybenzotriazole (932 mg, 6.9 mmol) and benzotriazol-1-yloxy-tris(dimethylamino)phosphonium hexafluorophosphate (3.05 g, 6.9 mmol) and stirred at room temperature for 5 d. The reaction mixture was evaporated under vacuum and the residue was purified by repeated flash chromatography (silica gel, 6×21 cm, 3–10% methanol in chloroform; silica gel, 6×21 cm, 60–100% ethyl acetate in hexane) to give 2.20 g (89%) of product contaminated with a small amount of HMPA (from BOP reagent): $^1$ NMR (CDCl$_3$, 90 MHz) d 1.43 (s, 9H), 1.47 (s, 9H), 1.97–2.27 (m, 2H), 3.03 (d, 2H, J+7.5 Hz), 3.77–4.10 (m, 4H), 4.20–4.55 (m, 1H), 4.90–5.23 (m, 1H), 5.17 (s, 2H), 5.93 (d, 1H, J=7.5 Hz), 6.17 (br s, 2H), 6.83–8.17 (m, 13H), 8.87 (br s, 1H); MS (ES) m/e 714 (M+H)$^+$.

(vii) Canavaninyl-glycinyl-γ-benzyl-aspartyl-anilide hydrochloride

The protected peptide product(486 mg, 0.677 mmol) was treated with TFA at room temperature for 2 h. The reaction mixture was evaporated at reduced pressure. The residue was evaporated from toluene, twice from 4N HCl in dioxane and then from toluene to give the crude product as the hydrochloride salt which was used without further purification.

(viii) N$^\alpha$- Acetyl-canavaninyl-glycinyl-γ-benzyl-aspartyl-anilide

The crude salt from above was dissolved in DMF and neutralized with diisopropylethylamine. Acetic anhydride (64 µL, 0.677 mmol) was added and the resulting solution stirred at room temperature for 24 h. The reaction mixture was evaporated under vacuum and the residue purified by flash chromatography (silica gel, 4×20 cm, 20% methanol in chloroform) to give the product: $^1$H NMR (CD$_3$OD, 90 MHz) δ 2.02 (s, 3H), 2.15 (t, 2H, J=6.0 Hz), 2.93–3.17 (m, 2H), 3.83–4.10 (m, 4H), 4.27–5.13 (m, 2H+HOD), 5.20 (s, 2H), 6.83–7.93 (m, 10 H); MS (ES) m/e 466 (M+H)$^+$.

(ix) N$^\alpha$-Acetyl-canavaninyl-glycinyl-aspartyl-anilide

The protected peptide from above was dissolved in methanol with 5% Pd/C and treated with hydrogen (Parr reactor, 50 psi, room temperature) for 4 h. The reaction mixture was filtered through a pad of Celite® and evaporated at reduced pressure. The residue was then evaporated from a mixture of toluene and methanol to give 190 mg of crude product. Part of this material (96 mg) was purified by partition chromatography (G-25, 2.5 cm×1 m) eluted with the upper phase of n-butanol:acetic:water (4:1:5) to give 47.6 mg of pure product: ES(FAB) m/e 466 [M+H]$^+$, m/e 464 [M-H$^-$; HPLC k' 2.29 [5µPRP-1: Hamiliton, 4.6×250 mm, flow=1.5 mL/min, UV detection at 220 nm, 88:12 (0.1% trifluoroacetic acid (aqueous): 0.1% trifluoroacetic acid in acetonitrile)]; HPLC k' 2.79 [5µPRP-1: Hamiliton, 4.6×250 mm, flow=1.5 mL/min, UV detection at 220 nm, gradient elution (0.1% trifluoroacetic acid (aqueous) :0.1% trifluoroacetic acid in acetonitrile ) start at 95:5, to 20 min. 50:50, hold for 5 min, return in 5 min. to 95:51; ] TLC R$_f$ 0.23 (silica gel, 4:1:1 butanol:acetic acid:water); TLC R$_f$ 0.42 (silica gel, 1:1:1:1 butanol:acetic acid:water:ethyl acetate).

Example 6

4[[N-Methyl-N-[3-(4-Pyridinyl)propanoyl]amino] acetyl]-2,2-[1,2-phenylenebis(oxy)]bisacetic Acid i) N-(Carbobenzyloxy)adrenolone To a solution of adrenolone hydrochloride (28.6 g, 0.121 mol) in 2N sodium hydroxide (200 mL) stirred at 5° C. were added simultaneously dropwise, separate solutions of benzyl chloroformate (20.6 g, 0.121 mol) in toluene (18 mL) and 2N sodium hydroxide (60 mL). The resulting solution was stirred 75 min at 5° C., diluted with water (230 mL) and acidified with 1N hydrochloric acid (536 mL). After stirring the resulting suspension for 30 min, the pale green solid which formed was filtered, stirred in water (180 mL) and filtered again. The filter cake was stirred briefly in ethanol (135 mL), filtered and air-dried. The solid was triturated with ethanol (135 mL), filtered and vacuum dried to yield the title compound (28.6 g, 75%): mp 183-6° C. $^1$H NMR (250 MHz, MeOD$_4$) δ 7.35(m, 7H), 6.83 (d, 1H), 5.1 (s, 2H), 4.55 (s, 2H).

ii) 4-[[N-(Carbobenzyloxy)N-methylamino]acetyl]-2,2'-[1,2-phenylenebis(oxy)]bisacetic Acid Dimethyl Ester A mixture of the compound of Example 6(i) (23.6 g, 0.0748 mol), acetone (340 mL), and anhydrous potassium carbonate (21.0 g) was heated to reflux for 70 min under Argon. The resulting suspension was cooled to RT and treated dropwise with methyl bromoacetate (29.0 g, 0.189 mol). The suspension was stirred 16 h at RT, at 50° C. for 6 h, cooled and filtered. The filtrate was concentrated and the residue was dissolved in dichloromethane (800 mL). The solution was washed with water (160 mL), 5% aqueous potassium carbonate (2×100 mL) and dried (sodium sulfate). Concentration gave the title compound (26.35 g, 82.3%): mp 56-9° C.; MS (DCI, NH$_3$) m/e 446 [M+H]$^+$; $^1$NMR (250 MHz, CDCl$_3$)δ 7.55 (d, J=8.5, 1H), 7.5(s, 1H), 7.4 (m, 5H), 6.85 (d, J=8.5, 1H), 5.15 (s, 2H), 4.80 (s, 2H), 4.77 (s, 2H), 4.7 (d, 2H), 3.80 (s, 6H). Anal. (C$_{22}$H$_{23}$NO$_9$.3/8H$_2$O) calcd: C, 58.44: H, 5.29: N, 3.10. found: C, 58.44: H, 5.13: N, 2.94.

iii) 4-[(N-Methylamino)acetyl]-2,2'-[1,2-phenylenebis(oxy)]bisacetic acid Dimethyl Ester Hydrochloride A solution of the compound of Example 6(ii) (5.0 g., 11.7 mmol) in absolute methanol (150 mL) was treated with 1M hydrogen chloride in diethyl ether (12 mL), 10% palladium on carbon was added and the suspension hydrogenated (10 psi) at RT. After five min, the mixture was filtered and the filtrate concentrated to yield the title compound (3.6 g, 94%): mp>197° C. (dec); $^1$H NMR (250 MHz, MeOD$_4$) δ 7.65 (d, J=8.5, 1H), 7.56 (s, 1H), 7.05 (d, J=8.5, 1H), 4.88 (s, 2H), 4.85 (s, 2H), 4.5 (s, 2H), 3.75 (s, 6H).

iv) 4-[[N-Methyl-N-[3-(4-pyridyl)propanoyl]amino]acetyl]-2,2'-[1,2-phenylenebis(oxy)]bisacetic Acid Dimethyl Ester 3-(4-Pyridyl)propanoic acid (0.75 g, 5 mmol) was refluxed in thionyl chloride (6 mL) for 12 min. The mixture was concentrated and concentrated twice from toluene. The resulting yellow solid was suspended in dichloromethane (10 mL) and added dropwise under argon to a cooled solution of the compound of Example 6(iii) (1.6 g, 5 mmol) in dichloromethane (50 mL) containing diisopropylethylamine (1.9 g, 15 mmol). The light amber solution was stirred under argon at RT for 20 h. The mixture was washed with water and brine, and the organic phase was dried (magnesium sulfate) and concentrated. The residual oil was purified by chromatography (silica gel, 2% methanol/dichloromethane). Fractions containing product were combined and concentrated to yield the title compound (0.66 g, 30%) as a white solid: MS (ES) m/e 459(M+H)$^+$; $^1$H NMR (400 MHz, CDCl$_3$) δ 2.75 (t, J=6.7 Hz, 2H), 3.0 (t, J=6.7 Hz, 2H), 3.05 (s, 3H), 3.75 (s, 6H), 4.7 (m, 2H), 4.75 (s, 2H), 6.85 (d, J=8.5 Hz, 1H), 7.15 (d, J=6.5 Hz, 2H), 7.5 (s, 1H), 7.6 (d, J=8.5 Hz, 1H), 8.45 (d, J=6.5 Hz, 2H).

v) 4-[[N-Methyl-N-[3-(4-pyridyl)propanoyl]amino]acetyl]-2,2'-[1,2-phenylenebis(oxy)]bisacetic Acid A solution of the compound of Example 6(iv) (0.2 g, 0.43 mmol) in 10% aqueous acetic acid was refluxed for 35 h. The mixture was concentrated and the residue was purified by HPLC (YMC ODS AQ, 50×250 mm; 90 mL/min, 15% CH$_3$CN/H$_2$O/0.1% TFA, UV detection at 220 nm). Product fractions were combined, concentrated to a small volume and lyophilized to give the title compound (92 mg, 50%) as a fluffy white hygroscopic solid: MS (ES) m/e 431(M+H)$^+$; $^1$H NMR (400 MHz, MeOD$_4$) δ3.05 (t, J=6.7 Hz, 2H), 3.15 (s, 3H), 3.25 (t, J=6.7 Hz, 2H), 4.75 (s, 2H), 4.85 (s, 2H), 4.8 (s, 2H), 7.0 (d, J=8.5 Hz, 1H), 7.55 (s, 1H), 7.65 (d, J=8.5 Hz, 1H), 7.95 (d, J=6.5 Hz, 2H), 8.65 (d, J=6.5 Hz, 2H). Anal. (C$_{21}$H$_{22}$N$_2$O$_8$.1.5 TFA.2H$_2$O) calcd: C, 46.53; H, 4.15;N, 4.52. found: C, 46.33; H, 4.27; N, 4.66

Example 7

N$^\alpha$Benzoyl-N$^A$[(cyanoimino)(phenoxy)methyl]-N$^\alpha$MeOrn-Gly-Asp-phenyl amide i) N$^\alpha$Carbobenzyloxy-N$^\alpha$methyl-Orn(Phth)

N$^\alpha$Cbz-Orn(Phth) was converted, by analogy with the method described in J. Org. Chem. 1983, 48, 77 to give the title compound.

ii) N$^\alpha$Carbobenzyloxy-N$^\alpha$MeOrn(Phth)-Gly Methyl Ester

A solution of the compound of Example 7(i) (9 g, 22 mmol), glycine methyl ester hydrochloride (3.5 g, 27.8 mmol), 1-hydroxybenzotriazole (3.66 g, 27 mmol), diisopropylethylamine (8 mL, 18 mmol) and 1-(3-dimethylaminopropyl)-3-ethylcarbodiimide hydrochloride (5.13 g, 26.8 mmol) in dimethylformamide (50 mL) was stirred overnight. The mixture was diluted with water, extracted with ethyl acetate and the organic phase was washed with dilute hydrochloric acid and with dilute sodium carbonate, dried (magnesium sulfate) and concentrated to yield the title compound (8.3 g).

iii) N$^\alpha$MeOrn(Phth)-Gly Methyl Ester

A solution of the compound of Example 7(ii) (25.0 g, 51 mmol) in methanol (150 mL) was treated with 15 drops of concentrated hydrochloric acid and 10% palladium on carbon (5.0 g). The mixture was shaken in a hydrogen atmosphere for 5 h. The mixture was filtered and the filtrate was concentrated to yield the title compound (21.0 g, quant).

iv) N$^\alpha$Benzoyl-N$^\alpha$MeOrn(Phth)-Gly Methyl Ester

A solution of the compound of Example 7(iii) (20.0 g, 58 mmol) in dichloromethane (150 mL) was treated with diisopropylethylamine (22.3 g, 0.17 mol) and stirred in an ice bath. The mixture was treated with a solution of benzoyl chloride (8.46 g, 60 mmol) in dichloromethane (20 mL), stirred for 1 h and washed with 3N hydrochloric acid. The organic phase was dried (magnesium sulfate) and concentrated to yield the title compound (23.6 g, 83%).

v) N$^\alpha$Benzoyl-N$^\alpha$MeOrn(Phth)-Gly

A solution of the compound of Example 7(iv) (23 g, 47 mmol) in acetone (250 mL), water (200 mL) and concentrated hydrochloric acid (40 mL) was heated to reflux for 24 h, cooled, diluted with water and extracted with ethyl acetate. The organic phase was dried (magnesium sulfate) and concentrated to yield the title compound (20 g, 90%).

vi) N$^\alpha$Benzoyl-N$^\alpha$MeOrn(Phth)-Gly-Asp(O-Bzl)-phenyl amide

A mixture of the compound of Example 7(v) (15.0 g, 32 mmol), Asp(O-Bzl)-phenyl amide (12.7 g, 32 mmol), 1-hydroxybenzotriazole (6.07 g, 45 mmol), diisopropylethylamine (8.32 g, 64 mmol) and 1-(3-dimethylaminopropyl)-3-ethylcarbodiimide hydrochloride (6.68 g, 35 mmol) in dimethylformamide (70 mL) was stirred overnight. The mixture was diluted with water, extracted with ethyl acetate and the organic phase was washed with cold 3N hydrochloric acid, dried (magnesium sulfate), and concentrated. The residue was chromatographed (silica gel, 3% methanol (/dichloromethane) to yield the title compound (12 g, 44%): MS m/e 718.2 [M+H]⁺.

vii) N$^\alpha$Benzoyl-N$^\alpha$MeOrn(Phth)-Gly-Asp-phenyl amide

The compound of Example 7(vi) (5.0 g, 5.8i mmol) was dissolved in ethanol (100 mL) with warning. It was treated with 10% palladium on carbon (2.0 g) which had been washed with aqueous acetic acid and filtered. The mixture was shaken in a hydrogen atmosphere for 15 h, filtered and the filtrate was concentrated to yield the title compound (4.4 g, 88%).

viii) N$^\alpha$Benzoyl-N$^\alpha$MeOrn-Gly-Asp-phenylamide

A solution of the compound of Example 7(vii) (4.4 g, 6.7 mmol) in ethanol (60 mL) was treated with hydrazine (1.0 g, 20 mmol), heated to reflux for 1 h, cooled and concentrated to yield the crude title compound: MS (FAB) m/e 498 [M+H]⁺.

ix) N$^\alpha$Benzoyl-N$^\Delta$[(cyanoimino)(phenoxy)methyl]-N$^\alpha$MeOrn-Gly-Asp-phenylamide A mixture of the compound of Example 7(viii) (2.0 g, 4.5 mmol) and diphenyl cyanocarbonimidate (1.25 g, 5.3 mmol) in isopropanol (40 mL) was stirred overnight, filtered and the filtrate was concentrated. The residue was chromatographed (silica gel, 4%–8%–15% methanol/dichloromethane containing 0.2% of acetic acid) to yield the title compound (0.7 g, 25%): MS (ESI) m/e 642.2 [M+H]⁺.

Example 8

N$^\alpha$Benzoyl-N$^G$cyano-N$^\alpha$MeArg-Gly-Asp-phenylamide

A solution of the compound of Example 7(ix) (0.3 g, 0.46 mmol) of was dissolved in methanol (20 mL), cooled and treated with a stream of ammonia for 5 min. The mixture was stirred overnight at RT, concentrated and the residue was dissolved in methanol (2 mL) and treated with acetic acid until the pH was approximately 5. The solution was diluted with ether to yield the title compound as a white solid (0.24 g, 92%: MS m/e 565.2 [M+H⁺.

Example 9

N-[N$^\alpha$-Benzoyl-N$^\Delta$-(1H-imidazol-2-yl)-N$^\alpha$-methyl-Orn-Gly]-3-(2-benzothiazolyl)-β-alanine (i) 3-(2-Benzothiazolyl)-β-alanine Cyclohexyl Ester a) 2-[[3-(Cyclohexyloxycarbonyl)2-[[(1,1-dimethylethoxy)carbonyl]amino]propanoyl]amino]phenyl disulfide A mixture of N-Boc-Asp β-cyclohexyl ester (3.2 g, 10 mmol), 2-aminophenyl disulfide (3.0 g, 12 mmol), isobutyl chloroformate (1.44 g, 14.2 mmol) and 4-methylmorpholine (1.326 g, 10 mmol) in tetrahydrofuran was stirred overnight. The residue was dissolved in dichloromethane, washed with water, dried and concentrated at reduced pressure. The residue was chromatographed (silica gel, 30% ether/petroleum ether). Fractions containing the title compound were combined, washed with 1N hydrochloric acid, washed with water, dried and concentrated to give the title compound (3.8 g, 90%): TLC R$_f$ 0.26 (silica, 7:3 petroleum ether:ether).

b) 3-(2-Benzothiazolyl)-3-(1,1-dimethylethoxycarbonyl) amino-propanoic Acid Cyclohexyl Ester The compound of Example 9(i)(a)(3.1 g, 3.7 mmol) and acetic acid were heated to 50° C. and zinc powder (5.6 g) was added in 15 min intervals. The hot mixture was filtered, the filtrate was concentrated and the residue was chromatographed (silica gel, 30% ether/petroleum) to give the title compound (2.2 g, 74%): TLC R$_f$ 0.42 (silica, 7:3 petroleum ether:ether).

c) 3-Amino-3-(2-benzothiazolyl)propanoic Acid Cyclohexyl Ester

The compound of Example 9(i)(b) (6.9 g, 17 mmol) and hydrogen chloride in dioxane (110 mL) was stirred overnight, concentrated and the residue was treated with toluene and concentrated to yield the title compound (5.7 g, 98%): TLC R$_f$ 0.4 (silica, 97:3 dichloromethane:methanol); MS (DCI/NH$_3$) 305 [M+H]⁺.

ii) N-[N$^\alpha$-Benzoyl-N$^\alpha$-methyl-Orn(Phth)-Gly]-3-(2-benzothiazolyl)-β-alanine Cyclohexyl Ester A mixture of the compound of Example 7(v) (5.0 g, 11 mmol), the compound of Example 9(i)(c) (3.0 g, 11 mmol), 1-(3-dimethylaminopropyl)-3-ethylcarbodiimide hydrochloride (2.95 g, 15.4 mmol), diisopropylethylamine (3.9 mL, 22 mmol), and 1-hydroxybenzotriazole (2.1 g, 15.5 mmol) in dimethylformamide was stirred overnight. The mixture was concentrated, diluted with water and extracted with dichloromethane. The organic phase was washed with water, dried and concentrated. The residue was chormatographed (silica gel, 5% methanol/dichloromethane) to yield the title compound (3.2 g, 40%).

iii) N-[N$^\alpha$-Benzoyl-N$^\alpha$-methyl-Orn-Gly]-3-(2-benzothiazolyl)-β-alanine Cyclohexyl Ester The compound of Example 9(ii)(3.2 g, 4.4 mmol) and hydrazine hydrate (0.33 g) were stirred in methanol (27 mL) for 72 h. The mixture was concentrated and the residue was chromatographed by HPLC (Ultrasphere ODS, 41 mm×250 mm, 60 mL/min, 35% acetonitrile/water/0/1% trifluoroacetic acid, UV detection at 254 nm) to yield the title compound (1.7g, 65%).

(iv) N-(2,2-Dimethoxyethyl)-2-methyl-2-pseudothiourea a) N-(2,2-Dimethoxyethyl)thiourea Methanol (200 mL) was saturated with ammonia and stirred with isothiocyanatoacetaldehyde dimethyl acetal (5.0 g) for 2 h. The mixture was concentrated and the residue was chromatographed (silica gel, 5% methanol/dichloromethane) to give the title compound.

b) N-(2,2-Dimethoxyethyl)-2-methyl-2-thiopseudourea

The compound of Example 9(iv)(a)(5.9 g) and iodomethane in acetonitrile was stirred overnight, concentrated, dissolved in dichloromethane, dried and concentrated to give the title compound.

v) N-[N$^\alpha$-Benzoyl-N$^\alpha$-methyl-N$^\Delta$-[[2,2-dimethoxyethyl)amino]thiocarbonyl)]-Orn-Gly]-3-(2-benzothiazolyl)-β-alanine Cyclohexyl Ester The compound of Example 9(iii) (1.6 g, 27 mmol) and the compound of Example 9(iv) (1.1 g, 3.9 mmol) were stirred with diisopropylethylamine (1.3 mL, 7.3 mmol) in dimethylformamide. The mixture was concentrated and the residue was dissolved in water. The solid which precipitated was extracted into dichloromethane and the organic phase was washed with water, dried and concentrated. The residue was chromatographed (silica gel, 5% methanol/dichloromethane) to yield the title compound (1.2 g, 63%).

vi) N-[N$^\alpha$-Benzoyl-N$^\Delta$-(1H-imidazol-2-yl)-N$^\alpha$-methyl-Orn-Gly]-3-(2-benzothiazolyl)-β-alanine Cyclohexyl Ester The compound of Example 9(v)(1.2 g) was stirred in 50% aqueous trifluoroacetic acid (50 mL) for 28 h and concentrated. The residue was purified by HPLC (Ultrasphere ODS, 41 mm×250 mm, 60 mL/min, gradient, A:acetonitrile B:water/0.1% trifluoroacetic acid, 10%–80% acetonitrile, UV detection at 254 nm) to give the title compound (0.2 g).

vii) N-[N$^\alpha$-Benzoyl-N$^\Delta$-(1H-imidazol-2-yl)-N$^\alpha$-methyl-Orn-Gly]-3-(2-benzothiazolyl)-β-alanine The compound of Example 9(vi) was treated with hydrogen fluoride and anisole to give the title compound.

Example 10

4[[-N-methyl-N-[5-(2-Aminobenzimidazolyl)]-amino]acetyl]2,2'[1,2-phenylenebis(oxy)]bisacetic Acid i) 4-[[N-Methyl-N-(3,4dinitrobenzoyl)amino]acetyl]-2,2'-[1,2-phenylenebis(oxy)]bisacetic Acid Dimethyl Ester A solution of 3,4-dinitrobenzoic acid (1.1 g, 4.5 mmol) in thionyl chloride (10 mL) was refluxed for 3 h. The reaction was cooled, concentrated, concentrated a few times from dichloromethane and dried at reduced pressure for 0.5 h. The residue was dissolved in dichloromethane (5 mL) and was added dropwise to a solution of the compound of Example 6(iii) (1.45 g, 4.0 mmol) in dichloromethane (25 mL) containing diisopropylethylamine (4.0 mL, 13.5 mmol). The mixture was stirred at RT for 1.5 h. The mixture was washed with dilute hydrochloric acid, 5% sodium bicarbonate, brine, dried (magnesium sulfate) and concentrated. The residue was purified by flash chromatography (silica gel, dichloromethane: methanol, 99:1) to give the title compound (650 mg, 33%): MS (FAB) m/e 520 [M+H]$^+$. $^1$H NMR (250 MH$_z$, CDCl$_3$) δ 8.08 (s, 1H), 8.0 (d, 1H), 7.9 (s, 1H), 7.60 (d,J=8.5, 1H), 7.54 (s, 1H), 6.9 (d, J=8.5, 1H), 4.9 (s, 2H), 4.82 (s, 2H), 4.79 (s, 2H), 3.8 (s, 6H), 3.0 (s, 3H).

ii) 4-[[N-Methyl-N-(3,4-diaminobenzoyl)amino]acetyl]-2, 2'-[1,2-phenylenebis(oxy)bisacetic Acid Dimethyl Ester Dihydrochloride A solution of the compound of Example 10(i) (440 mg, 0.8 mmol) in methanol (20 mL) and dichloromethane (5 mL) containing 1M ethereal hydrogen chloride (1.0 mL) was treated with 10% palladium on carbon (100 mg) and hydrogenated (50 psi) for 7 h. The mixture was filtered and the filtrate concentrated to yield the title compound (0.4 g, 94%): MS(ES) m/e 460 [M+H]$^+$.

iii) 4[[N-methyl-N-[5-(2-Aminobenzimidazolyl)]amino] acetyl]-2,2'-[1,2-phenylenebis(oxy)]bisacetic Acid Dimethyl Ester A solution of the compound of Example 10(ii) (400 mg, 0.7 mmol) in water (10 mL) and methanol (5 mL) was neutralized to pH 7.0 with 5% aqueous sodium carbonate followed by the addition of cyanogen bromide (75 mg, 0.7 mmol). The mixture was stirred at RT overnight. The methanol was evaporated, the aqueous phase was basified with 10% aqueous sodium hydroxide to pH 10.0 and the product was extracted with ethyl acetate. The organic phase was dried (magnesium sulfate), concentrated and the residue was chromatographed (silica gel, 93:7 dichloromethane:methanol) to give the title compound (100 mg, 31%): MS(ES) m/e 485 [M+H]$^+$, 483 [M-H]$^-$.

iv) 4-[[N-methyl-N-[5-(2-Aminobenzimidazolyl)]amino] acetyl]-2,2'-[1,2-phenylenebis(oxy)]bisacetic Acid Ditrifluoroacetate The compound of Example 10(iii) was heated to reflux in 10% aqueous acetic acid (10 mL) for 24 h. The mixture was concentrated and the residue was treated with trifluoroacetic acid and purified by preparative MPLC (ODS column, 30% methanol/water) to yield the title compound (39 mg, 28%): MS (ES) m/e 457 M+H]$^+$, 455 [M-H]$^-$; $^1$H NMR (250 MH$_z$, MeOD4) δ 7.75 (d, J=8.5, 1H), 7.6 (s, 1H), 7.48 (s, 1H), 7.4 (m, 2H), 7.28 (s, 1H), 7.05 (d, J=8.5, 1H), 5.0 (s, 2H), 4.8 (s, 2H), 4.76 (s, 2H), 3.05 (s, 3H).
Anal. (C$_{21}$H$_{20}$N$_4$O$_8$.2TFA.$^2$/3 H$_2$O) calcd: C, 43.11; H, 3.88; N, 8.04; found: C, 43.11; H, 3.66; N, 8.09.

Example 11

N-[N-[4-[(Aminoiminomethyl)hydrazono]butanoyl]-N-methyl-glycl]-3-(2-benzothiazolyl)-β-alanine i) N-(3-Carboxypropanoyl)-N-methyl-glycine Benzyl Ester A mixture of sarcosine benzyl ester (3.0 g, 30.7 mmol) and succinic anhydride (5.5 g, 30.7 mmol) in toluene (75 mL) was heated to reflux for 3 h, cooled, filtered, and the filtrate was concentrated. The residue was taken up in 5% aqueous sodium carbonate and extracted with ethyl acetate. The aqueous phase was adjusted to pH 3 with concentrated hydrochloric using Congo Red paper and extracted with ethyl acetate. The organic phase was washed with water, dried (magnesium sulfate) and concentrated to yield the title compound (7.4 g, 67.5%): TLC R$_f$ 0.48 (silica, 9:1:1 dichloromethane:methanol:formic acid).

ii) N-[(3-Ethylthiocarbonyl)propanoyl]-N-methyl-glycine Benzyl Ester

A mixture of the compound of Example 11(i) (7.4 g, 28 mmol), ethanethiol (1.76 g, 28.3 mmol), 1-(3-dimethylaminopropyl)-3-ethylcarbodiimide hydrochloride (5.4 g, 28 mmol), diisopropylethyl e (6 mL, 34 mmol), 4-dimethylaminopyridine (3.42 g, 27 mmol), and 1-hydroxybenzotriazole (3.42 g, 28 mmol) in dimethylformamide was stirred overnight. The mixture was concentrated, dissolved in dichloromethane and washed with water. The organic phase was dried (magnesium sulfate), concentrated and the residue was chromatographed (silica gel, dichloromethane) to give the title compound (4.8 g, 55%): TLC R$_f$ 0.13 (silica, 95:5 dichloromethane:methanol).

iii) N-[(3-Formyl)propanoyl]-N-methyl-glycine Benzyl Ester

To a solution of the compound of Example 11(ii) (1.2 g) and triethylsilane (1.37 g, 11.8 mmol) in acetone (30 mL) was added 10% Pd/C in portions. The mixture was filtered, the filtrate was concentrated and the residue was chromatographed (silica gel, 5% methanol/dichloromethane) to yield the title compound (0.72 g, 75%): TLC R$_f$ 0.24 (silica, dicloromethane); MS (DCI/NH$_3$) 264 [M+H]$^+$.

iv) N-[4[(Aminoiminomethyl)hydrazono]butanoyl]-N-methyl-glycine Benzyl Ester

A solution of the compound of Example 11(iii) (0.6 g, 2.4 mmol) in ethanol was treated with aminoguanidine nitrate (0.5 g, 3.7 mmol) and the mixture was warmed on a steam bath. The mixture was cooled and the solid which precipitated was filtered, washed with acetone, ether and with water. The solid was treated with dichloromethane and concentrated to yield the title compound (0.65 g, 65%): MS (DCI/NH$_3$) 320 +H+]$^+$.

v) N-[4-[(Aminoiminomethyl)hydrazono]butanoyl]-N-methyl-glycine

The compound of Example 11(iv)(0.5 g, 2.6 mmol), potassium carbonate (0.36 g, 2.6 mmol), water (2 mL) and tetrahydrofuran (5 mL) were stirred overnight. The mixture was concentrated, dissolved in water and the pH adjusted to 6 with 1N hydrochloric acid. The mixture was concentrated and the residue was treated with toluene and concentrated to yield the title compound (0.3 g, 50%): TLC R$_f$ 0.13 (silica, 9:1:1 dichloromethane:methanol:formic acid); MS (DCI/NH$_3$) 230 [M+H]$^+$.

vi) N-[N-[4-[(Aminoiminomethyl)hydrazono]butanoyl]-N-methyl-glycyl]-3-(2-benzothiazolyl)-β-alanine Cyclohexyl Ester A mixture of the compound of Example 11(v) (0.4 g, 1.7 mmol), the compound of Example 9(i) (0.53 g, 1.7 mmol), 1-(3-dimethylaminopropyl)-3-ethylcarbodiimide hydrochloride (0.33 g, 1.7 mmol), diisopropylethylamine (0.7 mL, 7.3 mmol), and 1-hydroxybenzotriazole (0.23 g, 1.7 mmol) in dimethylformamide (30 mL) was stirred at room temperature overnight. Hydrogen chloride in dioxane was added to pH 5, followed by dicyclohexylcarbodiimide (0.35 g). The mixture was stirred overnight, concentrated, diluted with water and extracted with dichloromethane. The organic phase was dried, concentrated and the residue was chromatographed (silica gel, 10% methanol/dichloromethane) and thin layer chromatographed (silica gel) to give the title compound(50 mg, 15%): MS (ESI) 516 [M+H]$^+$.

vii) N-[N-[4[(Aminoiminomethyl)hydrazono]butanoyl]-N-methyl-glycyl]-3-(2-benzothiazolyl)-β-alanine The compound of Example 11(vi)(30 mg, 0.06 mmol) dissolved in tetrahydrofuran (5 mL) and methanol (5 mL) was treated with potassium carbonate (12 mg) in water and stirred overnight. The mixture was concentrated and the residue was purified by HPLC (Dynamax, gradient A:acetonitrile B:water/0.1% trifluoroacetic acid, 13–50% acetonitrile) and lyophilized to give the title compound (1.4 mg): MS (ESI) 434 [M+H]+.

Example 12

Cyclo-(S,S)-(2-mercapto)benzoyl-($N^\alpha$-methyl)-4-aminomethyl-phenylalanyl-glycyl-aspartyl-(2-mercapto)-phenylamide [cyclo(S,S-Mba-MeAmf-Gly-Asp-Manl (i) $N^\alpha$-tert-butyloxycarbonyl-$N^\alpha$-methyl-p-iodophenylalanine $N^\alpha$-tert-butyloxycarbonyl-p-iodophenylalanine was converted to $N^\alpha$-tert-butyloxycarbonyl-$N^\alpha$-methyl-p-iodophenylalanine by analogy with the method described in Can. J. Chem. 55, 906 (1977).

(ii) $N^\alpha$-tert-butyloxycarbonyl-$N^\alpha$-methyl-4-aminomethyl-phenylalanine $N^\alpha$-tert-butyloxycarbonyl-$N^\alpha$-methyl-p-iodophenylalanine was converted to $N^\alpha$-tert-butyloxycarbonyl-$N^\alpha$-methyl-4-aminomethyl-phenylalanine by analogy with the method described in Syn. Commun. 21,2103 (1991).

(iii) $N^\alpha$-tert-butyloxycarbonyl-$N^\alpha$-methyl-4-CBZ-aminomethyl-phenylalanine $N^\alpha$-tert-butyloxycarbonyl-$N^\alpha$-methyl-4-aminomethyl-phenylalanine was converted to $N^\alpha$-tert-butyloxycarbonyl-$N^\alpha$-methyl-4-CBZ-aminomethyl-phenylalanine by analogy with the method described in J. Am. Chem. Soc. 76, 5552 (1954) to give the titled compound. $^1$H NMR (CDCl$_3$, 360 MHz) δ 1.1–1.4 (d, 9H), 2.6–2.7 (d, 3H), 2.8–3.3 (br, 2H), 4.2–4.4 (d, 2H), 4.4–4.6, 4.7–4.9 (br, 1H), 5.0–5.2 (s, 2H), 6.9–7.4 (br, 9H), 9.4–9.7 (br, 1H); MS (ES) m/e 443.2 [M+H]+;
HPLC k' 12.7 (5p Altex Ultrasphere ODS, 4.5mm×25 cm, gradient, A:acetonitrile B: water- 0.1% trifluoroacetic acid, 5%–50% acetonitrile in 20 min, UV detection at 220 nm); [α]D –67° (c 30, CHCl$_3$).

(iv) Boc-Asp (O-cHex)-Man(4-MBzl)

To a cold solution of Boc-Asp(O-cHex), (31.5 g, 100 mmol) in THF (500 mL) and N-methylmorpholine (13.1 g, 120 mmol), isobutylchloroformate (15.6 mL, 1.2 mmol) was added dropwise. The reaction mixture was stirred for a few minutes and a solution of Man(4-MBzl) (22.0 g, 96 mmol) in THF (500 mL) was added. The reaction mixture was allowed to warm to room temperature and stirred for 18 h. Upon completion of the reaction, the reaction mixture was filtered and the filtrate was concentrated to dryness. The residue was dissolved in ethyl acetate (500 mL), and washed successively with 5% aqueous citric acid (3×150 mL). water (1×400 mL), 10% aqueous NaHCO$_3$ (1×400 mL), water (1×400 mL) and saturated salt solution (1.·.300 mL). The solution was dried (anhydrous K$_2$CO$_3$), filtered and concentrated to yield the titled compound (53 g).

(v) Asp (O-cHex)-Man(4-MBzl)

Boc-Asp(O-cHex)-Man(4-MBzl) (52 g) was treated with 50% TFA/methylene chloride (400 mL) for 45 min at room temperature. The solvent was evaporated and chased several times with methylene chloride to eliminate traces of TFA. The product precipitated as its TFA salt upon addition of ether. The solid was collected and air dried to yield a white solid (46.7 g, 88%).

(vi) Boc-Gly-Asp(O-cHex)-Man(4-MBzl)

To a cold solution of Asp(O-cHex)-Man(4-MBzl) (46.7 g, 86.4 mmol) in DMF (100 mL) diisopropylethylamine (15 mL, 86.1 mmol) was added. N-Hydroxybezotriazole (14.0 g, 104 mmol) was added follwed by Boc-Gly (16.6 g, 94.8 mmol). The reaction mixture was stirred in the cold for a few minutes, and N-ethyl-N'(dimethylaminopropyl) carbodiimide (18.2 g, 94.9 mmol) was added. The reaction mixture was allowed to warm to room temperature and stirred for 18 h. The reaction mixture was concentrated to a small volume and poured into 1.5 L of aqueous 10% K$_2$CO$_3$. The precipitated product was collected by filtration and was washed with water to a neutral pH to afford the titled compound (50.6 g).

(vii) Gly-Asp(O-cHex)-Man(4-MBzl)

The compound of Example 12(vi) (11.7 g, 20 mmol) was treated with 50% TFA/CH$_2$Cl$_2$ (80 mL) as described in Example 4(b) to give 12.4 g of the titled compound.

(viii) Boc-Me-Amf(cBZ)-Gly-Asp(O-cHex)-Man(4-MBzl)

The compound of 12 (vii) was coupled to the compound of Example 12(iii) to provide the titled compound.

(ix) MeAmf(cBZ)-Gly-Asp(O-cHex)-Man(4-MBzl)

The compound of Example 12(viii) was treated with 50% TFA/CH$_2$Cl$_2$ as in Example 12(v) to provide the TFA salt of the titled compound.

(x) Mba(SEt)MeAmf(cBZ)-Gly-Asp(O-cHex)-Man(4-MBzl)

The compound 12(ix) was coupled to Mba(SEt) as in Example 12(vi) to provide the titled compound.

(xi) Cyclo-(S,S)-Mba MeAmf-Gly-Asp-Man

The protected linear peptide of Example 12(x) (0.25 g, 0.25 mmoL), was treated with anhydrous HF (10 mL) and anisole (1 mL) at 0° C. for 1 hr. The HF was removed at 0° C. under vacuum, and the residue was washed with ether to yield a tan solid (0.116 g). Purification by flash chromatography (medium pressure ODS reversed-phase column, 25% acentonitrile/H$_2$O-0.1% TFA) gave 0.069 of purified material: MS (ES) m/e 622[M&N]+ HPLC R$^1$ 9.1 (Altex Ultrasphere ODS, 4.5 mm×25 cm, gradient A: acetonitrile B: water-0.1% trifluoroacetic acid, 10–50% acetonitrile in over 20 minutes, at 220 nm);

Example 13

Parenteral Dosage Unit Composition

A preparation which contains 20 mg of the compound of Example 4 as a sterile dry powder is prepared as follows: 20 mg of the compound is dissolved in 15 ml of distilled water. The solution is filtered under sterile conditions into a 25 ml multi-dose ampoule and lyophilized. The powder is reconstituted by addition of 20 ml of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 14

Oral Dosage Unit Composition

A capsule for oral administration is prepared by mixing and milling 50 mg of the compound of Example 4 with 75 mg of lactose and 5 mg of magnesium stearate. The resulting powder is screened and filled into a hard gelatin capsule.

Example 15

Oral Dosage Unit Composition

A tablet for oral administration is prepared by mixing and granulating 20 mg of sucrose, 150 mg of calcium sulfate dihydrate and 50 mg of the compound of Example 4 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound of the formula (I):

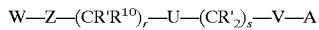  (I)

wherein:

A is

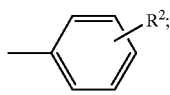

W is 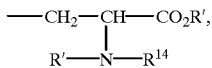;

Z is $(CH_2)_{1-2}$;

U and V independently are present as CO, $CR'_2$, $C(=CR'_2)$, $S(O)_r$, O, NR', CR'OR', $CR'(OR'')CR'_2$, $CR'_2CR'(OR'')$, $C(O)CR'_2$, $CR'_2C(O)$, CONR', NR'CO, OC(O), C(O)O, C(S)O, OC(S), C(S)NR', NR'C(S), $S(O)_rNR'$, $NR'S(O)_r$, N=N, NR'NR', $NR'CR'_2$, $NR'CR'_2$, $CR'_2O$, $OCR'_2$, C≡C, CR'=CR', or CR'(NR'R'')C(O);

each r independently is 0 to 3;

s is 0 to 2;

each R' independently is H, $C_{1-4}$alkyl, $C_{3-7}$cycloalky-$C_{0-4}$alkyl, or Ar-$C_{0-4}$alkyl;

each R" independently is R', —C(O)R', or —C(O)$OR^{15}$;

$R^{10}$ is H, $C_{1-4}$alkyl, or —NR'R';

each $R^{15}$ independently is $C_{1-4}$alkyl, $C_{3-7}$cycloalkyl-$C_{0-4}$alkyl, or Ar-$C_{0-4}$alkyl;

$R^2$ is present once or twice as $C_{1-4}$alkyl, J—$CO_2R'$, CONR', SR', NR'R", $C_{1-4}$alkoxy, hydroxy, CN, $CF_3$, halo, or $$-CH_2-\underset{\underset{R'-N-R^{14}}{|}}{CH}-CO_2R',$$

with the proviso that at least one $R^2$ is J—$CO_2R$; and

J is a single bond, —$OCR'_2$—, —$NR'CR'_2$—, $CR'_2$—$CR'_2$—, —$CR'_2$—, —CR'=CR', or —C(O)$NR'CR'_2$—;

each $R^{14}$ independently is $C_{1-4}$alkyl, $C_{3-7}$cycloalkyl-$C_{0-4}$alkyl, Ar-$C_{0-4}$alkyl, C(O)R', CN, $NO_2$, $SO_2R'$, or C(O)$OR^{15}$;

or a pharmaceutically acceptable salt thereof.

2. A compound according to claim 1 which is 4-[[N-methyl-N-[3-(4-pyridinyl)propionyl]amino]acetyl]-2,2'-[1,2-phenylenebis(oxy)]bisacetic acid or a pharmacetuically acceptable salt thereof.

3. A pharmaceutical composition comprising a compound according to claim 1 and a pharmaceutically acceptable carrier.

4. A method for effecting inhibition of platelet aggregation to a subject in need thereof which comprises administering a compound according to claim 1.

5. A method according to claim 4 for treating stroke.

6. A method according to claim 4 for treating transient ischemia attacks.

7. A method according to claim 4 for treating myocardial infarction.

8. A method for promoting reperfusion of an artery or vein and inhibiting reocclusion which comprises administering to a subject in need thereof a fibrinolytic agent and a compound according to claim 1.

* * * * *